United States Patent [19]

Scribner

[11] Patent Number: 5,219,366

[45] Date of Patent: Jun. 15, 1993

[54] ARTIFICIAL HAND

[76] Inventor: Albert W. Scribner, 6 Country Club Rd., Darien, Conn. 06820

[21] Appl. No.: 862,299

[22] Filed: Apr. 2, 1992

[51] Int. Cl.⁵ .............................................. A61F 2/66
[52] U.S. Cl. ...................................... 623/57; 901/39; 294/103.1; 623/64
[58] Field of Search ............... 623/57, 64, 65; 901/39; 414/729; 294/103.1, 104

[56] References Cited

U.S. PATENT DOCUMENTS

| 2,400,140 | 5/1946 | Sargeson | 623/65 |
| 4,332,038 | 6/1982 | Freeland | 623/64 |
| 4,623,183 | 11/1986 | Aomori | 901/39 |

Primary Examiner—Randy C. Shay

[57] ABSTRACT

A bi-directionally operable terminal device for an upper limb prosthesis is provided having a frame that includes a rigid finger portion which, to simulate the fingers of a natural hand, is partially curled in a manner generally corresponding in configuration and location to the normal relaxed finger condition of the natural hand; this rigid finger portion of said frame effectively constituting a first gripping jaw means. To said frame is attached a thumb-like unit that is adapted to swing towards and away from said rigid finger portion of the frame; this thumb-like unit including its immediately adjacent frame support structure effectively constituting a second jaw means. Operatively disposed between said thumb-like unit and said rigid finger portion of the frame, for bi-directional gripping movement, is the hooked forward end of a finger slide that is movably carried by said frame; this hooked forward end of said finger slide effectively constituting a third or central jaw means. The said first, second and third jaw means are disposed in substantially linear array. Forward movement of said finger slide (the third jaw means) enables an object to be gripped between said hooked end of the finger slide, (the third jaw means) and the rigid finger portion of said frame (the first jaw means) while rearward movement of said finger slide enables an object to be gripped between said thumb-like unit (the second jaw means) and said hooked end of the finger slide. A portion of the thumb-like unit is positionally indexible relative to the remaining part of the thumb-like unit; and further the thumb-like unit as a whole is adapted to be activated in response to the actuation of said finger slide. Separate corresponding and cooperating index fingers are provided on said finger portion of said frame and on said forward end of said finger slide respectively. The synergistic operation of the combination of these features affords a significantly wider variety of gripping modes for the present improved terminal device.

18 Claims, 3 Drawing Sheets

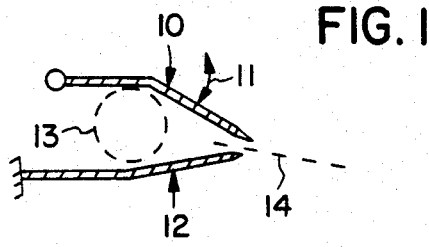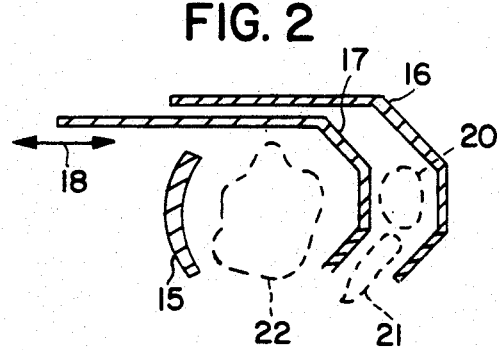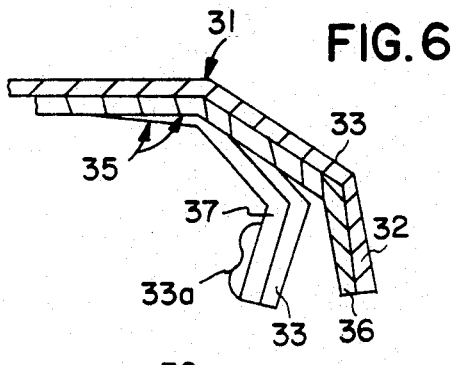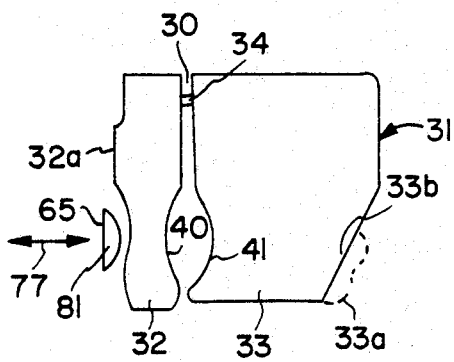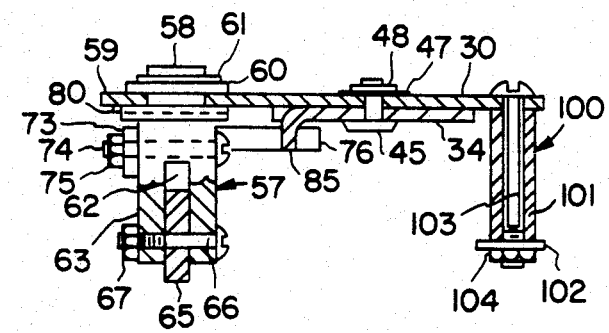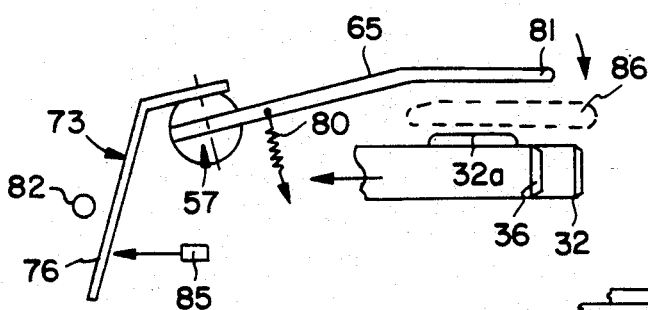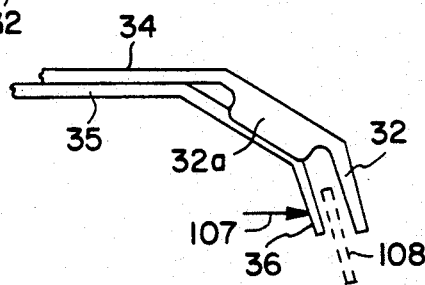

ARTIFICIAL HAND

BACKGROUND OF THE INVENTION

Terminal devices for conventional upper limb prostheses usually afford only one or two gripping modes. For example typical body-powered hook type terminal devices are capable of finger tip and key type modes of grip but are not as well suited for holding larger cylindrical type objects or objects that have tapered or other odd shaped configurations. The usual terminal devices associated with myoelectric prostheses afford a basic three-chuck type of grip mode but for the most part can additionally accommodate only objects that are larger than the minimum size opening between the closed thumb and finger elements of this type of terminal device. Such limited variety of gripping actions or modes normally associated with conventional terminal devices thus restricts the range of object holding activities that can be conveniently carried out by a prosthesis wearer.

Many attempts have been made to increase the functional versatility of terminal devices but such attempts even where partially successful have to varying degrees rendered such devices too heavy or mechanically complex for practical use. This condition represents just another example of the supremely difficult task associated with designing a terminal device that possesses most of the desired characteristics and features, such as being lightweight, strong, aesthetically acceptable, functionally versatile, relatively low cost, durable, mechanically simple and easy to maintain. Further it is most desirable that such a device be easy to repair in the field with simple tools by personnel needing very little in the way of skilled training. As may be readily appreciated many of these structural and functional objectives become virtually mutually exclusive in attempts for their attainment and such accounts in large measure for the relatively slow progress over the years in significantly enhancing the mechanical efficiency of such terminal devices.

SUMMARY OF THE INVENTION

The present invention contemplates increasing the variety and efficiency of the gripping modes afforded by a terminal device for an upper limb prosthesis while still maintaining an acceptable level of aesthetics. Prior art techniques for developing the grip actions in any given device have basically involved the use of two opposed and cooperating jaws, one or both of said jaws being movable towards and away from the other jaw. This type of gripping action however does not allow much deviation from the limited mechanical pattern of mutual cooperation between the two jaws and as a result the variety of different grip modes possible remains rather limited.

Conceptually the present invention contemplates the provision of three generally linearly aligned and cooperating jaw means; one such jaw means being effectively disposed between the other two jaw means. In this type of gripping arrangement the central jaw means is capable of being bi-directionally displaced towards either of the other two jaw means so as to selectively cooperate with either of the latter respectively. In this way objects may be held between the central jaw means and one or the other of said two other two jaw means. The structural incorporation of this bi-directional gripping concept into a terminal device involves the provision of (a) a rigid type finger simulating portion which effectively constitutes the first jaw means, (b) a thumb-like unit, including its immediately adjacent support structure, which effectively constitutes the second jaw means, and (c) a central slide having a forward hooked finger portion that effectively constitutes the third jaw means which is movable in one direction so as to cooperate with said thumb-like unit (the second jaw means), or in the opposite direction so as to cooperate with the said rigid finger simulating portion (the first jaw means). As will be later seen this bi-directional gripping action of the central movable hooked finger or third jaw means greatly increases the variety and efficiency of the gripping modes attainable through use of such an arrangement. Further gripping enhancement is obtained (a) by making the thumb-like unit (i) positionally indexible, and (ii) movable in response to the movement of the said central hooked finger, and (b) by providing a separate index finger on the said rigid frame finger portion for cooperation with a corresponding index finger on the end of the movable central hooked finger portion for mutual facial and lateral cooperation therebetween. The present terminal device structurally incorporates this bi-directional gripping action and the noted related features in such a way as to satisfy a significant number of the desired structural and functional characteristics for a terminal device as listed above in the BACKGROUND OF THE INVENTION.

DESCRIPTION OF THE DRAWINGS

FIG. 1 is a diagrammatic view illustrating the structural and functional nature of a conventional two-jaw type of gripping system.

FIG. 2 is a diagrammatic view illustrating the general structural and functional nature of the linearly arrayed three-jaw bi-directionally operated gripping system of the present invention.

FIG. 6 is a partial sectional view taken along section line 6—6 of FIG. 3.

FIG. 7 is a partial sectional view taken along section line 7—7 of FIG. 3.

FIG. 8 is an end elevation view taken from the right side of FIG. 4.

FIG. 9 is a partial sectional view taken along section line 9—9 of FIG. 3.

FIG. 10 is a fragmentary front elevation view of a portion of the side of the index finger near the outer end of the rigid frame finger portion.

FIGS. 11, 12 and 13 are diagrammatic views respectively illustrating the operation of various parts of the present apparatus; each view corresponding to the view taken in FIG. 5.

DETAILED DESCRIPTION OF THE INVENTION

Figure 3:
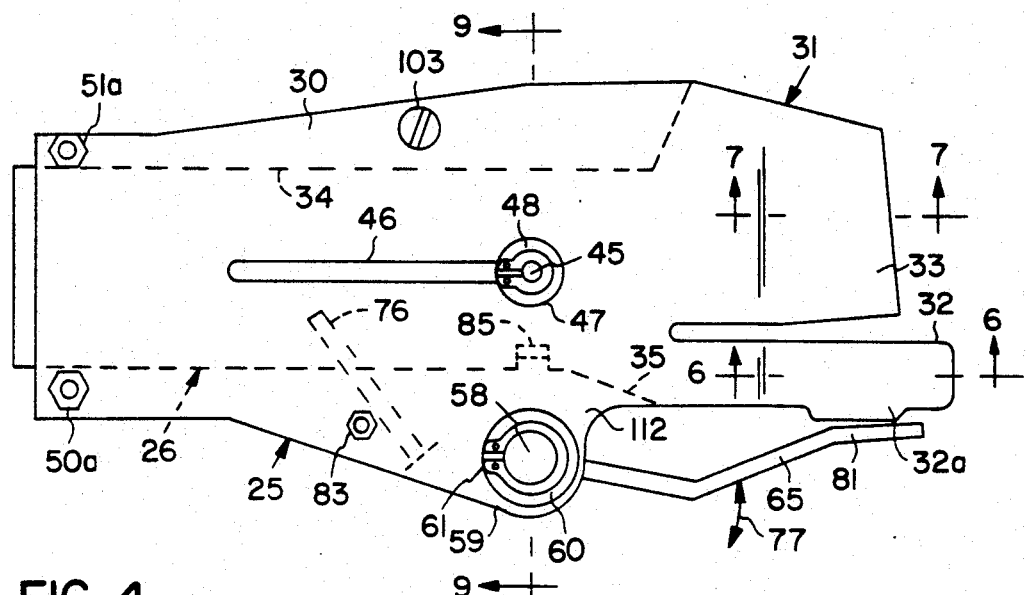
FIG. 3 is a top plan view of the present terminal device.

For the purposes of illustrating and describing the present invention it will be assumed that the prosthesis wearer requires a left hand terminal device. As will be apparent a corresponding mirror-image construction and operation may be used where a right hand terminal device is required. Further the invention described herein deals only with the hardware of the hand simulating portion of the prosthesis and does not include or present any aspect of the external or skin covering that would certainly be applied to the present hardware in order to give the prosthesis an outward appearance of a natural hand. As the disclosure progresses it should be noted that the overall external configuration of the present hardware profile has been made such that it duplicates fairly closely the overall natural hand profile or shape so that a person observing the back of the hand, the finger grouping and the upper portion of the thumb area would do so and not sense the artificiality of the hand. This outer profile duplication then makes it possible to attach to the hardware described herein an aesthetic covering of well known materials such as plastic, rubber, etc. which gives the appearance of being very authentic. The hereinafter described prosthesis mechanisms and access thereto are located on the palm side of the artificial hand facing the wearer's own body so as to thereby be only minimally observable.

Referring to FIG. 1 a conventional two-jaw type of grip system is illustrated wherein a pivoted finger simulating unit 10 constituting a first movable jaw is adapted as indicated by arrows 11 to swing towards and away from a rigid thumb-like unit 12 constituting a fixed second jaw so as to be thereby capable of gripping and holding either a larger type object such as 13 or a smaller flat type object such as 14. This two-jaw grip concept is illustrative of that effectively used in most conventional upper limb terminal devices such as the split hook type and myoelectric prostheses.

FIG. 2 diagrammatically illustrates the present concept of a three-jaw bi-directionally operated type of gripping system wherein a thumb unit and related abutment means 15, and a forward hook-like finger portion 16 effectively constitute second and first jaws respectively. A central third jaw or hook 17 which is effectively disposed between said first and second jaws is mounted for bi-directional rectilinear movement as indicated by arrows 18 into selective cooperation with the rigid finger portion 16 so as to grip and hold an object such as 20 or 21 therebetween or alternatively with the thumb unit and related abutment means 15 so as to grip and hold a larger object such as 22 therebetween. As will be seen from FIG. 2 the first, second and third jaw means 16, 15 and 17 are effectively disposed in substantially linear or serial array. The structural incorporation of this three-jaw bi-directional gripping concept into the present terminal along with additional improved structural and functional features will now be described with primary reference to FIGS. 3-9.

Figure 4:
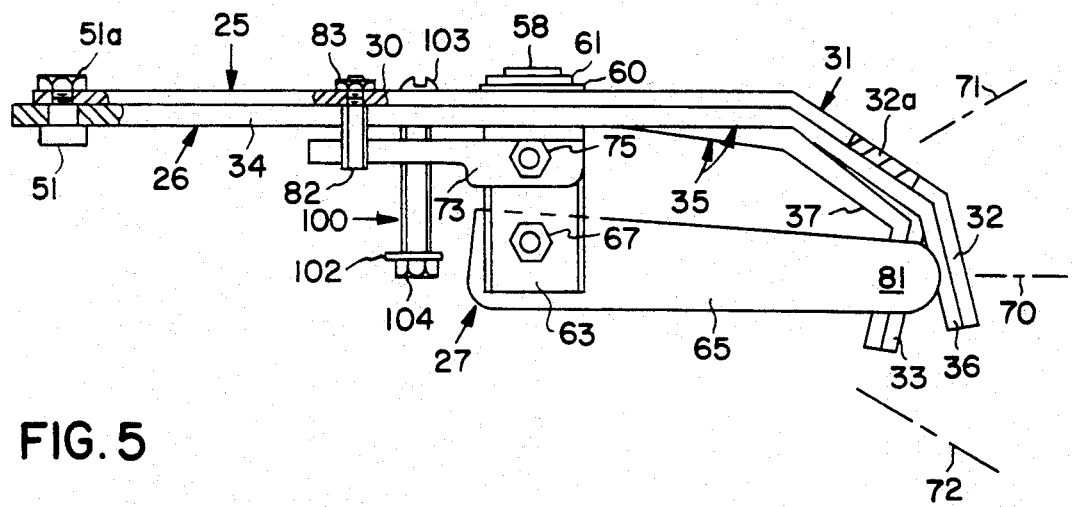
FIG. 4 is a front elevation view of the apparatus illustrated in FIG. 3.
Figure 5:
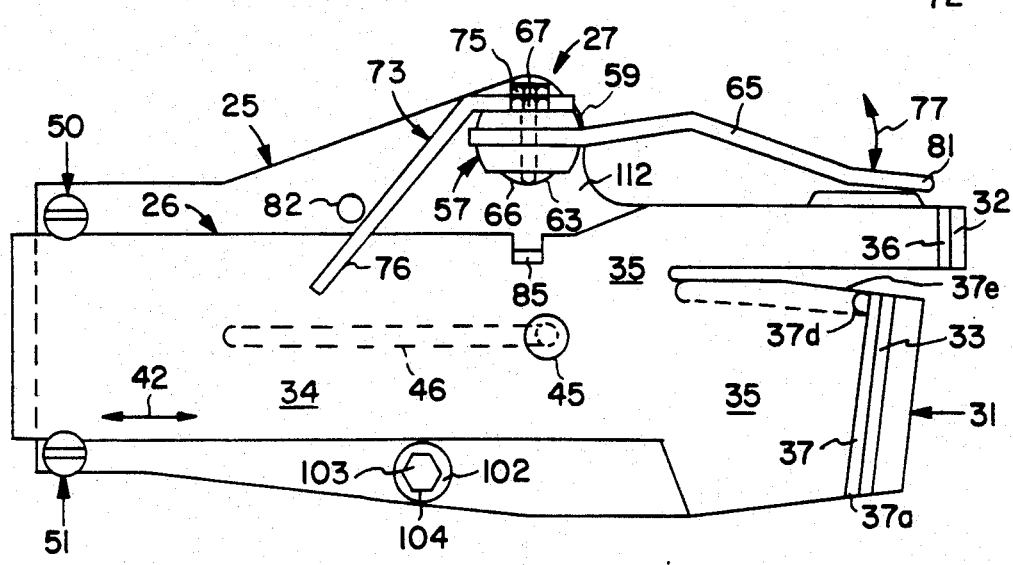
FIG. 5 is a bottom view of the apparatus illustrated in FIG. 4.

Referring to FIGS. 3-5 there is shown a terminal device generally comprising three major components namely a rigid frame 25, a finger slide 26 and a thumb-like unit 27; these mayor components 25, 26 and 27 corresponding respectively to the jaws 16, 17 and 15 diagrammatically illustrated and described in connection with FIG. 2. The rigid frame 25 comprises a base portion 30 corresponding to the back of the natural hand and an integral forward rigid finger portion 31, FIG. 3-5, corresponding to the position and configuration of the partially curled fingers of the normally relaxed condition of a natural hand. Said forward finger portion 31 has a separate index finger 32 formed thereon while the remaining solid integral part 33, FIGS. 3 and 7, thereof simulates the middle, ring and little fingers of the natural hand. The finger slide 26 comprises a shank or neck 34 and an integral forward or right hand end 35 as viewed in FIG. 4. Said forward end 35 of the slide 26 is also formed with a separate index finger 36, FIG. 6, the remaining part 37 of said slide end 35 also simulating said middle, ring and little fingers of the natural hand. The forward right hand faces of said finger slide end 35 have configurations and locations which are conjugally substantially the same as the rearward or left said faces of said finger portion 31 of the rigid frame 25; these relative configurations and locations thus allowing the said forward end 35 of the finger slide to move into substantial nesting relation with respect to the inner or left side of said finger slide portion 31 as is best illustrated in FIGS. 6 and 7. The outer or left side edge of the index finger 32, as viewed in FIG. 8, may be provided with a bent-off ear or pad 32a, FIGS. 3, 8 and 10, the purpose for will be subsequently described. Likewise the right side edge, as viewed in FIG. 8, of said remaining finger portion 33 may be provided with a notched bent-off ear 33a, FIGS. 7 and 8, the purpose for which will also be later described. For ease of illustration the ear 33a has been shown in FIG. 8 as being swung approximately 90 degrees from its actual operative position illustrated in FIG. 10 and into the plane of FIG. 8. The index finger 32 is also formed with a concave recess 40 as shown in FIG. 8 while said remaining finger portion 33 is corresponding and cooperatively recessed as at 41 as as also shown in FIG. 8. The said index finger 36 and the remaining finger portion 37 on the finger slide 26 are similarly recessed, which recesses will hereinafter be referred to and designated as 40a and 41a respectively.

The finger slide 26 is reciprocally mounted on the frame 25 for rectilinear movement as indicated by arrows 42 of FIG. 5, i.e. forwardly or to the right and rearwardly or to the left as viewed in FIGS. 3-5, by means including a short stud 45, FIGS. 3, 5 and 9, which extends through a suitable hole in the shank or neck 34 of the finger slide 26 and into and through the forward end of a rearwardly extending slot 46, FIGS. 3 and 5, formed in the base portion 30 of the frame 25. The upper end of the stud 45, as seen in FIG. 9, is provided with a washer 47 and any suitable securing means such as a cotter pin or a retaining snap ring 48, FIGS. 3 and 9, or the like. On the frame base portion 30 is threadedly secured two shoulder screws 50 and 51, FIGS. 4 and 5, which have heads the inner peripheral portions of which, as best seen in FIG. 5, respectively overlie one of the two opposite parallel side edges of the neck 34 of said finger slide 26 and which are secured to base 30 by the respectively associated nuts 50a and 51a, FIGS. 3 and 4. As will be apparent the finger slide 26 is thus supported and guided for rectilinear forward and rearward sliding movement 42, FIG. 5, on the frame 25 in accordance with the course and length of said frame slot 46.

The thumb-like unit 27 of the present terminal device comprises a generally cylindrical hub 57, FIGS. 5 and 9, that has an integral upper reduced neck or shaft 58, FIGS. 3, 4 and 9, that extends through a suitable hole formed in said frame base portion 30; this hole being located in the laterally offset portion 59, FIGS. 3 and 5, of said frame base portion 30 so as to simulate the general pivot position for a natural thumb. The said shaft 58 is rotatably retained on said frame portion 59 by means of a washer 60, FIGS. 3, 4 and 9, and any suitable securing means such as a cotter pin or a conventional type snap fastener ring 61 or the like. The lower portion of the hub 57 is diametrically slotted as at 62 of FIG. 9 and is formed with opposed flat outer walls such as 63 that are substantially parallel to the plane of said slot 62. Pivotally mounted in the slot 62 is the left hand end, as seen in FIG. 4, of a thumb member 65 that extends forwardly towards the extremities of index finger 32 and the remaining finger portion 33 of the frame 25. A pivot screw 66, FIGS. 5 and 9, extends through the hub 57 and the thumb member 65 and is provided with a nut 67, FIGS. 4 and 9, so that when tightened the screw and nut 66, 67 can frictionally clamp the thumb member 65 in the slot. Thus the thumb member 65 may be manually shifted to and frictionally retained in any one of several arcuate indexed positions between those respectively illustrated by lines 70, 71 and 72 of FIG. 4, relative to the rigid frame finger portion 31; the purpose for which will be later described. Any suitable stop means may be provided for limiting the extent of the indexible movement possible for the thumb member 65 from the normal position 70 to the positions indicated by the limiting maximum displacement 71 and 72.

A control lever or crank 73, FIG. 5, is secured to the outer wall 63 of hub 57 by means of a screw 74 and an associated nut 75, FIGS. 4 and 9. The radially outer end 76, FIGS. 3, 5 and 9, of lever 73 extends over and closely spaced from the adjacent flat surface of the neck or shank 34 of the finger slide 26 as is best seen in FIGS. 4, 5 and 9. As will now be apparent the thumb-like unit 27 generally comprising the hub 57, the thumb member 65 and the lever 73 is capable of oscillating movement on the frame 25 as indicated by arrows 77 of FIGS. 3, 5 and 8. Any suitable spring means such as torsion spring 80, diagrammatically illustrated in FIG. 9, and having its two ends respectively anchored in the adjacent frame portion 59 and the hub 57, may be provided to yieldably bias the thumb-like unit 27 as a whole in a clockwise direction as viewed in FIG. 5. The limit of this biased clockwise movement is determined by the engagement of either the outer radial end 81, FIGS. 3-5 and 8, of the thumb member 65 with the index finger 32 or by the engagement of the said outer portion 76 of the lever 73 with a stop stud 82, FIG. 5; the latter being secured on the lower side, as viewed in FIG. 4, of the frame base portion 30 by any suitable means such as by having its reduced and threaded upper neck extending through a suitable hole in said frame base position 30 and engaged by a lock nut 83, FIGS. 3 and 4. The rotative position of hub 57 will be substantially same for each such biased rotational limiting engagement; i.e. the thumb member end 81 will be substantially in engagement with finger pad 32a when lever end 76 engages said stop 82. As is best shown in FIGS. 5 and 9 the side edge of the shank or neck 34 of the finger slide 26 is formed with a 90 degree bent-off ear 85 whose rearward movement with the slide 26 is adapted to be intercepted by the outer end 76 of said crank or lever 73 of the thumb-like unit 27. An abutment post assembly 100, FIGS. 4, 5 and 9, is fixedly secured to the frame base portion 30; such post assembly comprising a tubular member 101, FIG. 9, and a washer 102 of a slightly larger outside diameter through both of which extends a threaded screw 103 that passes through a suitable hole in the frame base portion 30 and has an associated nut 104 at its lower end which is adapted to be tightened so as to securely fix the post assembly 100 in a position on the frame base portion 30 that is on the opposite side from and slightly rearwardly of the hub 57 of the thumb-like unit 27 as is best illustrated in FIG. 5.

The operation of the terminal device described above will now be explained primarily with reference to the diagrammatic illustrations in FIGS. 2, 11, 12 and 13. The normal condition of the parts is such that the finger slide 26 is in a forward position so that its forward end 35 is in substantial nesting relation with respect to the corresponding inner sides of said finger 32 and the remaining finger part 33 of the said rigid finger portion as is best seen in FIGS. 6 and 7. The normal frictionally retained indexed position for the thumb member 65 on the hub 57 is that shown in FIG. 4 and is designated therein by the line 70, while the normal spring biased rotative position of the thumb-like unit 27 as a whole is illustrated in FIGS. 3 and 5 wherein the outer end 81 of the thumb member 65 engages the side of said index finer 32, (note FIG. 8), and wherein the lever 73 is simultaneously in substantial engagement with the stop 82 as shown in FIGS. 3 and 5. From this normal condition of the parts the present terminal devide may be placed in four or five different modes for gripping different types of objects to be held. For example several finger tip modes of grip may be obtained by moving the finger slide 26 rearwardly from its said normal nesting condition so that various smaller types of objects may be received between the several different cooperating surfaces between the forward end of the finger slide 26 and the rigid frame finger portion 31 in a manner corresponding to that illustrated for objects 20 and 21 of FIG. 2; the finger slide 26 then being displaced forwardly to engage, grip and hold such objects. It will be noted from FIG. 8 that the cooperating gripping faces along the side edge 33b of said finger portion 33 and corresponding edge 37a, FIG. 5, on the slide end 35 may also be used to pick up and hold objects thus reducing the need for a wrist rotation action for the present terminal device. The noted forward displacement of finger slide 26, as designated by arrow 107, of FIG. 10, will also enable the cooperating index fingers 32 and 36 on the frame and slide respectively to grip and hold a small flat type objects 108, FIG. 10, such as a coin, a sheet of paper, etc. This index finger grip action is facilitated by the fact that said index fingers 32 and 36 extend somewhat forwardly as illustrated in FIG. 4 as opposed to the somewhat rearward disposition of the extremities of the remaining finger portions 33 and 37 as shown in FIGS. 4, 6 and 8 which are oriented so as to additionally form the general hook configuration, as is best seen in FIG. 7, for the slide 26 that facilitates the palm grip mode that will be described below.

Figure 12:
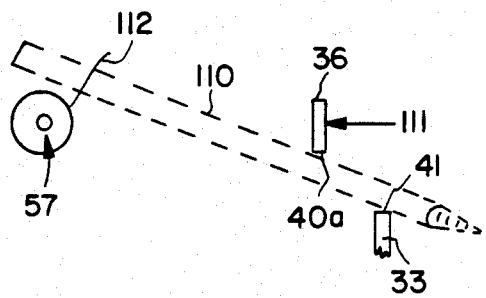

In said normal condition of the parts a pencil like object 110, FIG. 12, may be received between the similar cooperating recessed edges 40, 41, FIG. 8, respectively formed in the sides of said index finger 32 and remaining finger portion 33 of said slide 26. Upon movement of the finger slide in a rearward direction as indicated by arrow 111 of FIG. 12 said object 110 will be tightly clamped on one side thereof at two rigid points defined by the hub 57 and/or the related immediately adjacent frame portion 112, FIGS. 3, 5 and 12, and the upper recessed edge 41, as seen in FIG. 12, of said rigid frame finger portion 33, and on the other side thereof at a point defined by the lower recessed edge 40a as seen in FIG. 12 of the index finger 36 on the finger slide 26. This pencil type grip mode, which here does not require the direct use of the thumb member 65, is capable of holding a pencil, an eating utensil or similar objects exceptionally tight due to the angular camming action of the rearwardly moving finger 36, FIG. 12, with respect to the slightly angled relative orientation of the object 110 being held.

From the said normal condition of the parts, when a key mode type of grip is desired the thumb member 65 is first manually indexed from its normal position 70, FIG. 4, to a second frictionally held position 71, FIG. 4, wherein the end portion 81 of the thumb member 65 can laterally cooperate with the bent-off pad 32a on the side of the index finger 32, as illustrated by FIGS. 8, 10 and 11. The thumb member may at the same time be manually swung open as shown in FIG. 11 so that the lever 73 moves away from stop 82 as shown in FIG. 11 while said outer end 81 of the thumb member 65 is moving away from the said finger pad 32a all against the biasing action of the spring means 80. Here the swing-open movement of the thumb member 65 may be produced by the act of inserting the object 86, FIG. 11, between the thumb member and the finger pad 32a. If the gripping force produced by the action of said spring 80 is not sufficient to properly hold the object 86 then the finger slide 26 may be moved rearwardly so that its bent-off ear 85 moves into camming engagement with the end 76 of lever 73 thereby causing the lever 73 and thumb member 65 to apply a very substantial grip force to said object 86.

Figure 13:
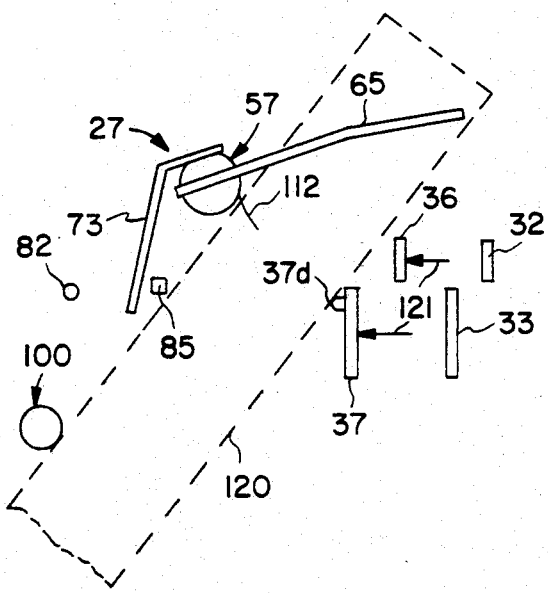

From said normal condition of the parts when a larger size object is to be tightly gripped and held in a palm grip mode wherein said object extends angularly across the palm area of the artificial hand the thumb member 65 is manually moved to a frictionally held indexed position 72, FIG. 4, whereafter the act of manually inserting the object 120, FIG. 13, into the palm area of the hand between the normally positioned index finger 36 and the hooked end portion 37 of the finger slide 26 on the one said thereof and the two abutment points on the other side thereof defined by the hub 57 and the post assembly 100 will cause the thumb member 65 to be swung wide open. This will result in the lever 73 being swung far away from the stop 82 and closer to the bent-off ear 85 on the normally positioned finger slide 26. Thereafter when finger slide 26 is moved rearwardly as indicated by arrows 121 of FIG. 13 the said remaining hooked finger portion 37 of the finger slide 26 will engage the object 120 at a point effectively located between said hub 57 and post assembly 100 and thus move said object into engagement with said hub 57 and said post assembly 100 as shown in FIG. 13. Depending on the size of the object 120 this rearward displacement of finger slide 26 may cause said bent-off ear 85 to cammingly engage lever end 76 so as to thereby swing the thumb member 65 against the object 120 on the nearest side the latter as viewed in FIG. 13 in order to further exert an object retention force. This latter condition effectively acts as a fourth grip action which serves to keep larger objects from being wedged out of the palm of the terminal device, i.e. in a direction towards the observer in FIG. 13. It should be noted in connection with this palm mode of grip that the jaw means 15, illustrated and discussed in convection with FIG. 2, is effectively defined in FIG. 13 by the thumb-like unit 27, its immediately adjacent frame portion 112 and by the post assembly 100. In order to insure a good palm gripping action the entire inner edge 37e, FIG. 5, of said finger portion 37 may be provided with an inwardly facing rib 37d, FIGS. 5 and 13 which engage the right side, as viewed in FIG. 13, of the object 120.

When the parts are in their said normal condition the said hooked portions 33 and 37 thereof, as best seen in FIG. 7, afford a convenient hook means for carrying items such as an attache case or the like. As is apparent any suitable locking means may be provided for locking the slide 26 in any given grip position thereof on the frame 25 as is well understood in the art.

It will be seen that the present terminal device incorporates the above described linearly arranged three jaw bi-directional gripping system and related features and as such affords a significantly greater variety of different grip modes all derived from a simple rectilinear displacement of the finger slide 26. This functional versatility however is not conditioned upon the presence of a lot of complex mechanical claptrap; rather the above described terminal device is made up of only three relatively simple main components namely the frame 25, the slide 26 and the thumb-like unit 27. A prototype similar to the described device, sized for a teenage person and using 0.080 inch or so thick aluminum sheet metal, will weigh approximately 4½ ounces or less; all three of said main components being very inexpensive to manufacture and with most maintenance and/or repairs therefor being carried out with exceptional ease using only the simplest of tools.

Figure 14:
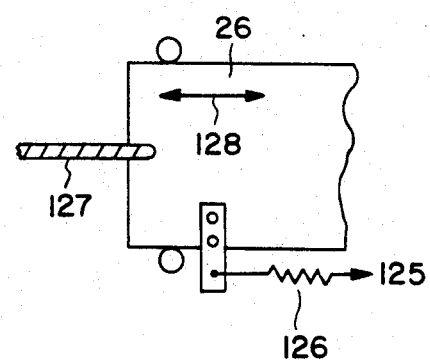
FIGS. 14 and 15 are diagrammatic views illustrating two different systems for power operating the present terminal device.
Figure 15:
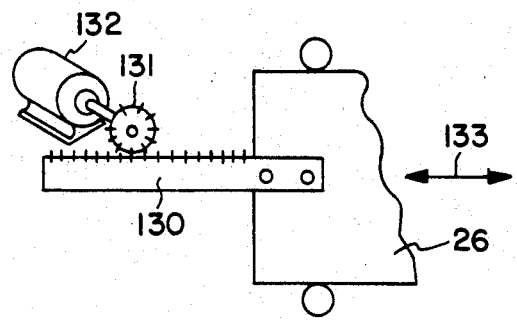

The present so-called Rachael Device may be actuated using either a conventional body-powered system or an electric motor drive means similar to those employed in current myoelectric type prostheses. More specifically FIG. 14 illustrates the use of a body-powered system wherein the finger slide 26 is normally biased in a forward direction 125 by means of a suitable spring means 126. A conventional type cable 127 is connected to the finger slide 26 so as, in combination with said spring means 126, to enable the finger slide 26 to be rectilinearly actuated as indicated by arrows 128, FIG. 14. It will be noted here that the rearward movement of finger slide 26 as effected by a pulling of the cable 127 will involve a "voluntary open" action with respect to the rigid frame finger portion 31 and a simultaneous "voluntary close" action with respect to the thumb-like unit 27 and post assembly 100. An electrical drive system is illustrated in FIG. 15 wherein a geared rack 130 fixedly secured to the finger slide 26 is provided with teeth that mesh with those of a pinion gear 131 which is adapted to be driven in either rotative direction by an electric motor 132 so as to rectilinearly actuate said rack 130 and slide 26 as indicated by arrows 133. The operation of motor 132 is governed by any suitable myoelectric or other known type of electrical control system.

What is claimed is:

1. An improved terminal device for an upper limb prosthesis: comprising a frame;

separate first, second and third jaw means effectively serially arranged on and carried by said frame;

said first and second jaw means being disposed in mutually spaced apart relation while said third jaw means is effectively disposed between said first and second jaw means; said first and third jaw means having corresponding index finger portions and remainder finger portions formed thereon, respectively; and means for movably mounting said third jaw means on said frame for movement in one direction so as to move said third jaw means into cooperative gripping relation with respect to said first jaw means, and for movement in the opposite direction so as to move said third jaw means into cooperative gripping relation with respect to said second jaw means.

2. Apparatus as defined by claim 1: additionally comprising drive means for actuating said third jaw means.

3. Apparatus as defined by claim 1: additionally comprising means mounting at least a portion of said second jaw means for movement relative to said frame; and means responsive to movement of said third jaw means for actuating said portion of said second jaw means.

4. A three-jaw bi-directionally operated terminal device for an upper limb prosthesis: comprising
a frame;
said frame including a forward finger portion that simulates the fingers of a natural hand and being partially curled in a manner generally corresponding in configuration and location to the normal relaxed finger condition of the natural hand;
thumb means carried by said frame and including a thumb member having one end that extends forwardly for gripping cooperation with said finger portion of said frame; means for movably mounting the other end of said thumb member on said frame so that said one end of said thumb member may move towards and away from a gripping condition with respect to said finger portion of said frame;
a finger slide carried by said frame and having a forward end that is arranged so that both the forward and rearward sides, respectively, thereof are capable in combination with said frame finger portion and said thumb means of applying a gripping force to an object to be held;
means for mounting said finger slide on said frame for forward and rearward sliding movement;
said forward end of said finger slide being effectively disposed between said thumb means and said finger portion of said frame whereby forward displacement of said finger slide moves its said forward end towards said finger portion of said frame and away from said thumb means so as to be thereby capable of gripping an object to be held between said forward end of said finger slide and finger portion of said frame, and whereby rearward displacement of said finger slide moves its forward end towards said thumb means and away from said finger portion of said frame so as to be capable of gripping an object to be held between said forward end of said finger slide and said thumb means; and
means responsive to the movement of said finger slide for actuating said thumb member.

5. Apparatus as defined by claim 4; additionally comprising means for yieldably biasing said thumb member in one direction of its movement.

6. Apparatus as defined claim 4: additionally comprising means for adjustably mounting said thumb member for selective movement to a plurality of operative indexed positions relative to the remaining portion of said thumb means.

7. Apparatus as defined by claim 4 wherein said finger portion of said frame includes a separate index finger, and wherein said finger slide also includes a separate index finger that is adapted to cooperatively move together with said slide towards and away from said separate index finger formed on said finger portion of said frame.

8. Apparatus as defined by claim 4 additionally comprising drive means for actuating said finger slide.

9. A terminal device for an upper limb prosthesis: comprising
a frame;
said frame including a forward finger portion that simulates the fingers of a natural hand and being partially curled in a manner corresponding to the normal relaxed condition of the natural hand;
thumb means carried by said frame and including a thumb member having one end thereof that extends forwardly for gripping cooperation with said finger portion of said frame;
means for movably mounting the other end of sid thumb member on said frame so that said one end of said thumb member may move towards and away from a gripping condition with respect to said finger portion of said frame;
a finger slide carried by said frame and having a forward end having a forward finger portion that is partially curled and has a configuration that substantially corresponds to the configuration of the partially curled finger portion of said frame; and
means mounting said finger slide on said frame for sliding movement in forward and rearward directions whereby the partially curled forward end of said finger slide may be moved respectively into and out of nesting relation with respect to the partially curled finger portion of said frame, this relative movement between the forward end of the said finger slide and said frame finger portion thus affording gripping and release actions for an object that is to be held between (a) said partially curled end of said finger slide, and (b) the partially curled finger portion of said frame and a portion of said thumb means.

10. Apparatus as defined by claim 9 wherein said partially curled finger portion of said frame is substantially rigid with respect to the rest of said frame.

11. Apparatus as defined by claim 9 wherein said finger portion of said frame includes a separate index finger, and wherein said forward end of said finger slide also includes a separate index finger that is adapted to cooperatively move forwardly towards and rearwardly away from said separate index finger on said finger portion of said frame.

12. Apparatus as defined by claim 9 wherein the partially curled forward end of said finger slide is effectively operatively disposed between said thumb means and said partially curled finger portion of said frame whereby forward displacement of said finger slide moves its partially curled forward end towards said partially curled finger portion of said frame and at the same time away from said thumb means so as to be capable of gripping an object to be held between said forward end of said finger slide and the partially curled finger portion of said frame, and whereby rearward displacement of said finger slide moves its forward end towards said thumb means and at the same time away from said partially curled finger portion of said frame so as to be capable of gripping an object to be held between said finger slide and said thumb means.

13. Apparatus as defined by claim 12: additionally comprising means mounting said thumb member on said frame for movement in a lateral direction with respect to the direction of said finger slide.

14. Apparatus as defined by claim 13: additionally comprising means responsive to the displacement of said finger slide for actuating said thumb member.

15. Apparatus as defined by claim 14 wherein the rearward movement of said finger slide is adapted to swing said one ene of said thumb member towards a gripping condition with respect to the side of said frame finger portion.

16. Apparatus as defined by claim 15: additionally comprising means for yieldably biasing said thumb member in one direction of its movement.

17. Apparatus as defined by claim 15 additionally comprising means for adjustably mounting said thumb member on said thumb meansb for movement to a plurality of operative indexed positions relative to the remaining portion of said thumb means.

18. Apparatus as defined by claim 12: additionally comprising drive means for actuating said finger slide.

* * * * *